US011612880B2

(12) United States Patent
Nagata et al.

(10) Patent No.: US 11,612,880 B2
(45) Date of Patent: Mar. 28, 2023

(54) METHOD FOR PRODUCING OXIDE CATALYST, AND METHOD FOR PRODUCING UNSATURATED NITRILE AND UNSATURATED ACID

(71) Applicant: ASAHI KASEI KABUSHIKI KAISHA, Tokyo (JP)

(72) Inventors: Dai Nagata, Tokyo (JP); Satoshi Miike, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 88 days.

(21) Appl. No.: 16/319,712

(22) PCT Filed: Aug. 8, 2017

(86) PCT No.: PCT/JP2017/028716
§ 371 (c)(1),
(2) Date: Jan. 22, 2019

(87) PCT Pub. No.: WO2018/030384
PCT Pub. Date: Feb. 15, 2018

(65) Prior Publication Data
US 2019/0262800 A1   Aug. 29, 2019

(30) Foreign Application Priority Data

Aug. 12, 2016   (JP) .............................. JP2016-158858

(51) Int. Cl.
| | |
|---|---|
| *B01J 21/08* | (2006.01) |
| *B01J 37/04* | (2006.01) |
| *B01J 37/08* | (2006.01) |
| *B01J 23/30* | (2006.01) |
| *B01J 35/02* | (2006.01) |
| *B01J 37/02* | (2006.01) |
| *C07C 51/215* | (2006.01) |
| *C07C 57/04* | (2006.01) |
| *C07C 253/24* | (2006.01) |
| *C07C 255/08* | (2006.01) |
| *C07C 51/21* | (2006.01) |
| *B01J 37/12* | (2006.01) |
| *B01J 23/18* | (2006.01) |
| *B01J 37/03* | (2006.01) |
| *B01J 23/28* | (2006.01) |
| *B01J 23/20* | (2006.01) |
| *B01J 23/00* | (2006.01) |
| *C07B 61/00* | (2006.01) |

(52) U.S. Cl.
CPC .............. *B01J 23/30* (2013.01); *B01J 21/08* (2013.01); *B01J 23/002* (2013.01); *B01J 23/18* (2013.01); *B01J 23/20* (2013.01); *B01J 23/28* (2013.01); *B01J 35/026* (2013.01); *B01J 37/0221* (2013.01); *B01J 37/0236* (2013.01); *B01J 37/03* (2013.01); *B01J 37/04* (2013.01); *B01J 37/08* (2013.01); *B01J 37/12* (2013.01); *C07C 51/21* (2013.01); *C07C 51/215* (2013.01); *C07C 57/04* (2013.01); *C07C 253/24* (2013.01); *C07C 255/08* (2013.01); *B01J 2523/00* (2013.01); *C07B 61/00* (2013.01); *Y02P 20/52* (2015.11)

(58) Field of Classification Search
CPC ...... B01J 21/08; B01J 35/026; B01J 37/0221; B01J 37/0236; B01J 37/04; B01J 37/08
See application file for complete search history.

(56) References Cited

U.S. PATENT DOCUMENTS

| | | | | |
|---|---|---|---|---|
| 3,657,155 A | * | 4/1972 | Yoshino et al. | ..... B01J 23/8435 502/247 |
| 4,590,175 A | * | 5/1986 | Sasaki | ..................... B01J 23/85 502/237 |
| 4,891,347 A | | 1/1990 | Oh-Kita et al. | |
| 4,968,838 A | | 11/1990 | Oh-Kita et al. | |
| 6,143,690 A | * | 11/2000 | Komada | .................. B01J 23/20 502/211 |
| 6,514,902 B1 | | 2/2003 | Inoue et al. | |
| 2008/0249328 A1 | | 10/2008 | Kaduk et al. | |
| 2010/0240921 A1 | | 9/2010 | Tateno et al. | |
| 2011/0207600 A1 | | 8/2011 | Kauffman et al. | |
| 2013/0253217 A1 | | 9/2013 | Ishii et al. | |
| 2013/0289298 A1 | | 10/2013 | Tateno et al. | |
| 2014/0114109 A1 | | 4/2014 | Sanchez Valente et al. | |
| 2015/0231604 A1 | | 8/2015 | Ishii et al. | |
| 2016/0297753 A1 | | 10/2016 | Ishii et al. | |

FOREIGN PATENT DOCUMENTS

| | | |
|---|---|---|
| CN | 1302227 A | 7/2001 |
| CN | 103269790 A | 8/2013 |
| CN | 103313966 A | 9/2013 |
| EP | 3278874 A1 | 2/2018 |
| EP | 3495043 A1 | 6/2019 |
| JP | 47-18722 B1 | 5/1972 |
| JP | 61-114739 A | 6/1986 |
| JP | 63-107745 A | 5/1988 |
| JP | 10-330343 A | 12/1998 |
| JP | 2001-300310 A | 10/2001 |
| JP | 2003-181287 A | 7/2003 |
| JP | 2003-210982 A | 7/2003 |

(Continued)

OTHER PUBLICATIONS

Machine-generated English Translation of Japanese Patent No. 2010-201365, published on Sep. 16, 2010.*

(Continued)

*Primary Examiner* — Matthew P Coughlin
(74) *Attorney, Agent, or Firm* — Birch, Stewart, Kolasch & Birch, LLP

(57) ABSTRACT

The present invention provides a method for producing an oxide catalyst containing antimony, comprising
a step (A) of obtaining the oxide catalyst using antimony particles containing a diantimony trioxide as a source of the antimony,
wherein an abundance of a pentavalent antimony in a surface layer of the antimony particle to be measured in XPS analysis is less than 70 atom %, and
the antimony particle has an average particle size of 1.2 µm or less.

13 Claims, 1 Drawing Sheet

(56) References Cited

FOREIGN PATENT DOCUMENTS

| JP | 2007-301470 A | 11/2007 |
|----|---------------|---------|
| JP | 4014863 B2 | 11/2007 |
| JP | 2010-201365 A | 9/2010 |
| JP | 2013-520316 A | 6/2013 |
| JP | 5707841 B2 | 4/2015 |
| KR | 91-8727 B1 | 10/1991 |
| KR | 10-2008-0102221 A | 11/2008 |
| KR | 10-2016-0068896 A | 6/2016 |

OTHER PUBLICATIONS

International Preliminary Report on Patentability and Written Opinion of the International Searching Authority, dated Feb. 12, 2019, for International Application No. PCT/JP2017/028716, with an English translation of the Written Opinion.
Al-Saeedi et al., "Bulk structure and catalytic properties of mixed Mo—V—Sb—Nb oxides for selective propane oxidation to acrylic acid," Journal of Catalysis, vol. 215, No. 1, Apr. 1, 2003, XP055237926, pp. 108-115.
International Search Report (PCT/ISA/210) issued in PCT/JP2017/028716, dated Oct. 17, 2017.
European Search Report for European Application No. 17839454.0, dated Jul. 9, 2019.
Reiche et al., "Monitoring Interface Interactions by XPS at Nanometric Tin Oxides Supported on Al2O3 and Sb2Ox," The Journal of Physical Chemistry B, vol. 108, 2004, pp. 9905-9913, 9 pages total.
Wang et al., "Effect of Preparation Method on Electrocatalysis of Rare Earth Gd Doping SnO2/Sb Electrode," Journal of Jilin University (Science Edition), vol. 43, No. 4, 2005, pp. 546-550, 5 pages total, with an English abstract.

\* cited by examiner

[Figure 1]
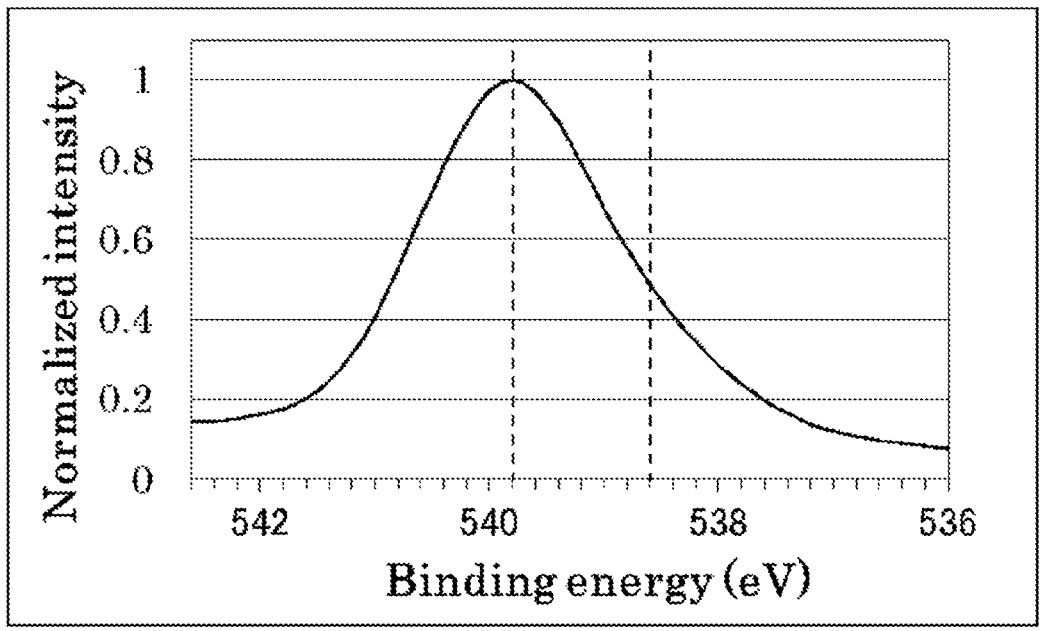
[Figure 2]
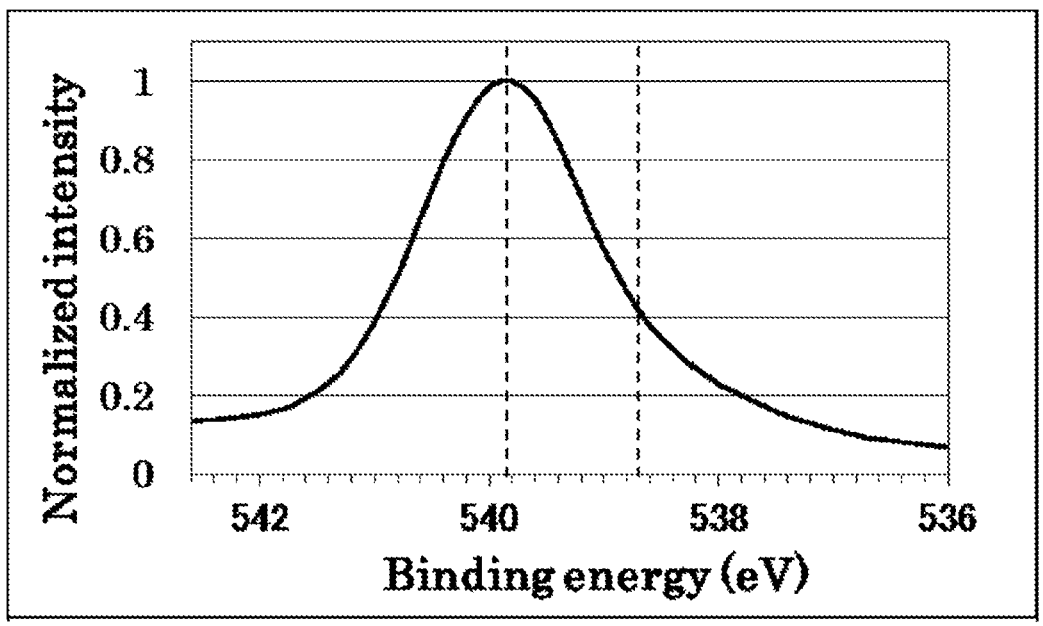

METHOD FOR PRODUCING OXIDE CATALYST, AND METHOD FOR PRODUCING UNSATURATED NITRILE AND UNSATURATED ACID

TECHNICAL FIELD

The present invention relates to a method for producing an oxide catalyst, and a method for producing an unsaturated nitrile and an unsaturated acid.

BACKGROUND ART

Conventionally, there is known a method in which, using an olefin such as propylene as a starting material, a corresponding unsaturated carboxylic acid or unsaturated nitrile is produced by a gas-phase catalytic oxidation reaction or ammoxidation reaction.

Meanwhile, in recent years, attention has been paid on methods in which, using an alkane such as propane as a starting material instead of an olefin such as propylene, a corresponding unsaturated acid or unsaturated nitrile is produced by a gas-phase catalytic oxidation reaction or ammoxidation reaction. Of such methods, various methods for producing a composite oxide catalyst containing Sb have been suggested.

Patent Literature 1, in which diantimony trioxide is used as the starting material for Sb in a composite oxide catalyst, discloses that diantimony trioxide having an average particle size of 1 µm or less is preferably used in order to improve the dissolution rate of Sb in an aqueous solvent.

As a technique for producing a composite oxide catalyst for an ammoxidation reaction in which propylene is employed as the starting material, Patent Literature 2 discloses use of antimony trioxide particles having an average particle size of 0.1 µm or more and less than 5 µm as the starting material of the Sb component. It is mentioned that setting the average particle size at 0.1 µm or more enables the intended product to be produced at a high selectivity and a catalyst having an excellent flowability to be obtained. It is also mentioned that setting the average particle size at less than 5 µm enables a catalyst having high catalyst activity and high selectivity of the intended product and having a high particle strength to be obtained.

CITATION LIST

Patent Literature

Patent Literature 1: Japanese Patent No. 4014863
Patent Literature 2: Japanese Patent No. 5707841

SUMMARY OF INVENTION

Technical Problem

However, the composite oxide catalyst disclosed in Patent Literature 1 has a lower yield of the reaction of producing acrylonitrile using propane as the starting material than the yield of the reaction of producing acrylonitrile using propylene as the starting material by use of the composite oxide catalyst disclosed in Patent Literature 2. Thus, a further improvement in the yield of the intended product is required.

The present invention has been made in view of the above situation, and it is an object of the present invention to provide a method for producing an oxide catalyst for a gas-phase catalytic oxidation or gas-phase catalytic ammoxidation reaction of propane or isobutane, the oxide catalyst enabling a corresponding unsaturated nitrile or unsaturated acid to be obtained from propane or isobutane at a high yield, and a method of producing an unsaturated nitrile and unsaturated acid by using the oxide catalyst.

Solution to Problem

The present inventors have intensively studied to solve the above problem of the conventional art, and, as a result, have focused on, with regard to antimony particles containing diantimony trioxide, which will be the starting material of a catalyst, pentavalent antimony present on the surface of particles (e.g., in the range up to 2 nm from the surface of the particles). As a result of the study, the inventors have found that an oxide catalyst that enables a high yield of an unsaturated nitrile or of an unsaturated acid to be achieved by using antimony particles having a ratio of pentavalent antimony present on the surface within a specific range and having a specific particle size as the starting material, thereby having completed the present invention.

That is, the present invention is as follows.

[1]
A method for producing an oxide catalyst comprising antimony, comprising
a step (A) of obtaining the oxide catalyst using an antimony particle comprising a diantimony trioxide as a source of the antimony,
wherein an abundance of a pentavalent antimony in a surface layer of the antimony particle to be measured in XPS analysis is less than 70 atom %, and
the antimony particle has an average particle size of 1.2 µm or less.

[2]
The method for producing the oxide catalyst according to [1], wherein, in the step (A), an oxide catalyst represented by following formula (1) is obtained:

$$Mo_1V_aNb_bSb_cX_dZ_eO_n \qquad (1)$$

wherein X represents at least one element selected from the group consisting of W, Bi, Mn, and Ti; Z represents at least one element selected from the group consisting of La, Ce, Pr, Yb, Y, Sc, Sr, and Ba; a, b, c, d, e, and n represent atomic ratios of respective elements, and $0.01 \leq a \leq 1.00$, $0.01 \leq b \leq 1.00$, $0.01 \leq c \leq 1.00$, $0.00 \leq d \leq 1.00$, $0.00 \leq e \leq 1.00$; and n is a value satisfying balance among a valence.

[3]
The method for producing the oxide catalyst according to [1] or [2], wherein, in the step (A), an oxide catalyst further comprising 20 to 70% by mass of silica, in terms of $SiO_2$, is obtained.

[4]
A method for producing an unsaturated nitrile, comprising a step of obtaining an oxide catalyst by the method for producing the oxide catalyst according to any of [1] to [3], and a production step of subjecting propane or isobutane and $NH_3$ to a gas-phase catalytic ammoxidation reaction in the presence of the oxide catalyst obtained to obtain the unsaturated nitrile.

[5]
A method for producing an unsaturated acid, comprising a step of obtaining an oxide catalyst by the method for producing the oxide catalyst according to any of [1] to [3], and a production step of subjecting propane or isobutane to a gas-phase catalytic oxidation reaction in the presence of the oxide catalyst obtained to obtain the unsaturated acid.

Advantageous Effects of Invention

According to the method for producing an oxide catalyst according to the present invention, it is possible to produce an oxide catalyst that enables an unsaturated nitrile or unsaturated acid to be obtained from propane or isobutane at a high yield.

BRIEF DESCRIPTION OF DRAWINGS

FIG. 1 shows the $Sb_{3d3/2}$ peak of diantimony trioxide particles in an XPS spectrum described in Example 1.

FIG. 2 shows the $Sb_{3d3/2}$ peak of diantimony trioxide particles in an XPS spectrum described in Comparative Example 1.

DESCRIPTION OF EMBODIMENTS

Hereinafter, an embodiment for carrying out the present invention (hereinafter, simply referred to as "present embodiment.") will be described in detail. The following present embodiment is illustrative for explaining the present invention, and is not construed as limiting the present invention to the following content. The present invention can be variously modified and performed within the gist thereof.

[Method for Producing Composite Oxide Catalyst]

The method for producing an oxide catalyst according to the present embodiment, which is a method for producing an oxide catalyst containing antimony, comprises a step (A) of obtaining an oxide catalyst using antimony particles containing diantimony trioxide as the source of the antimony, wherein the abundance of pentavalent antimony in the surface layer of the antimony particles to be observed in XPS analysis is less than 70 atom %, and the antimony particles have an average particle size of 1.2 µm or less. Since the method is configured in such a way, according to the method for producing an oxide catalyst according to the present embodiment, it is possible to produce an oxide catalyst that enables an unsaturated nitrile or unsaturated acid to be obtained from propane or isobutane at a high yield. Accordingly, an oxide catalyst obtained by the production method of the present embodiment can be suitably used for a gas-phase catalytic oxidation reaction or gas-phase catalytic ammoxidation reaction of propane or isobutane.

The method for producing an oxide catalyst according to the present embodiment preferably includes, in the step (A) mentioned above, a formulation step of dissolving or dispersing a starting material containing the antimony particles to thereby obtain a formulated starting material liquid (hereinafter, referred to also as "step (1)"), a drying step of drying the formulated starting material liquid to thereby obtain a dried material (hereinafter, referred to also as "step (2)"), and a calcination step of calcining the dried material to thereby obtain a calcined material (hereinafter, referred to also as "step (3)"). Herein, the "starting material" is not particularly limited as long as the starting material is a compound containing the antimony particles described above or other constituent elements of the oxide catalyst, but specifically, compounds described below can be used.

The step (A) may have a projection removal step of removing projections present on the particle surface of the calcined material to thereby obtain a main body of a catalyst (hereinafter, referred to also as "step (4)"), after the calcination step described above.

The calcined material or the main body of the catalyst obtained by removing the projections from the calcined material is used as the oxide catalyst.

[Composite Oxide]

In the step (A) in the present embodiment, it is preferable to obtain an oxide catalyst represented by the following formula (1):

$$Mo_1V_aNb_bSb_cX_dZ_eO_n \qquad (1)$$

wherein X represents at least one element selected from the group consisting of W, Bi, Mn, and Ti; Z represents at least one element selected from the group consisting of La, Ce, Pr, Yb, Y, Sc, Sr, and Ba; a, b, c, d, e, and n represent elemental ratios of the respective elements per element of Mo, and $0.01 \le a \le 1.00$, $0.01 \le b \le 1.00$, $0.01 \le c \le 1.00$, $0.00 \le d \le 1.00$, $0.00 \le e \le 1.00$; and n is a value satisfying balance among valences.

When the step (4) is carried out, the compositional ratio of the oxide catalyst may be a different value from the compositional ratio of the calcined material obtained after the calcination step. This is because a projection of an oxide catalyst to be described below has a composition different from that of the main body of the catalyst and the compositional ratio of the whole catalyst is also changed by removing the projection from the main body of the catalyst. Thus, the compositional ratio is set while taking the change into account in the step (1). Herein, the "projection" refers to matter effused and/or attached to a calcined material obtained by the calcination step mentioned below, or matter projected from and/or attached to the surface of the calcined material.

In the formula (1), a, which represents the elemental ratio of V per element of Mo, is $0.01 \le a \le 1.00$, preferably $0.075 \le a \le 0.70$, more preferably $0.10 \le a \le 0.40$. When a is in the above range, a more proper propane activity can be attained, and the decomposition of acrylonitrile tends to be more suppressed. Then, b, which represents the elemental ratio of Nb per element of Mo, is $0.01 \le b \le 1.00$, preferably $0.02 \le b \le 0.70$, more preferably $0.03 \le b \le 0.40$. When b is in the above range, a more proper propane activity can be attained, and the decomposition of acrylonitrile tends to be more suppressed. Further, c, which represents the elemental ratio of Sb per element of Mo is $0.01 \le c \le 1.00$, preferably $0.03 \le c \le 0.80$, more preferably $0.05 \le c \le 0.50$. When c is in the above range, the ammoxidation reaction more easily proceeds. Furthermore, a/c, which represents the elemental ratio of V to Sb is preferably $0.50 \le (a/c) \le 2.00$, more preferably $0.60 \le (a/c) \le 1.80$, still more preferably $0.70 \le (a/c) \le 1.60$. When a/c is in the above range, decomposition of acrylonitrile produced tends to be more suppressed.

In the formula (1), d, which represents the elemental ratio of X per element of Mo, is $0.00 \le d \le 1.00$, preferably $0.001 \le d \le 0.50$, more preferably $0.003 \le d \le 0.40$, still more preferably $0.005 \le d \le 0.30$. When d is in the above range, the decomposition activity of acrylonitrile can be more suppressed, and a more proper propane activity tends to be attained. X represents at least one element selected from the group consisting of W, Bi, Mn, and Ti. From the viewpoint of the industrial long-term use, X represents preferably an element of W, Bi or Mn, and more preferably an element of W because the decomposition of acrylonitrile tends to be suppressed.

In the formula (1), e, which represents the elemental ratio of Z per element of Mo, is $0.00 \le e \le 1.00$, preferably $0.0001 \leq e \leq 0.50$, and more preferably $0.0005 \leq e \leq 0.30$. When the e is in the above range, decomposition of acrylonitrile and combustion of ammonia tend to be more suppressed. Z represents at least one element selected from the group consisting of La, Ce, Pr, Yb, Y, Sc, Sr, and Ba.

[Carrier]

In step (A) in the present embodiment, it is preferable that an oxide catalyst carried by a carrier can be obtained. Examples of the component of a carrier by which the metal oxide component (hereinafter, referred to also as "composite oxide.") in the oxide catalyst is carried include, but are not particularly limited to, silica, alumina, zirconia, and titania. As for components of the carrier, one component may be used singly, or two or more components may be used in combination. A particularly preferable component of the carrier is silica. When the catalyst is carried by the carrier containing silica, the catalyst tends to have a high mechanical strength. Thus, the catalyst can be suitably used for a reaction including use of a fluidized-bed reactor, for example, a gas-phase catalytic ammoxidation reaction described below.

When the carrier contains silica, the content of silica in the oxide catalyst is, based on the total mass (100% by mass) of the composite oxide and the carrier, in terms of $SiO_2$, preferably 20% by mass or more and 70% by mass or less, more preferably 25% by mass or more and 65% by mass or less, and still more preferably 30% by mass or more and 60% by mass or less. The content of silica is, from the viewpoint of the strength and prevention of powdering, preferably 20% by mass or more. When the content of silica is 20% by mass or more, stable operation tends to be enabled for industrial use of the catalyst, the loss of the catalyst to be carried tends to be decreased, and this case is preferable also economically. Also from the viewpoint of obtaining a sufficient activity and making the amount of the catalyst required proper, the content of silica is preferably 70% by mass or less. Particularly when the catalyst is used for a fluidized-bed reaction, when the content of silica is 70% by mass or less, the specific gravity of the catalyst is appropriate and a good fluid state tends to be easily formed.

[Step (1): Formulation Step]

The step (1) in the present embodiment is a step of dissolving or dispersing a starting material in a liquid composed of water and/or a solvent to obtain a formulated starting material liquid. Examples of the solvent include, but are not limited to, alcohols such as methanol and ethanol, and ketones such as acetone and methyl ethyl ketone. As the liquid, which is not particularly limited, any of water, a solvent, and a mixed liquid of water and a solvent may be used. Water is more preferably used. As a starting material to be used in this case, an antimony source containing the antimony particles described above (hereinafter, referred to also as "starting material of Sb") is essential. Other starting materials are not particularly limited as long as the starting materials are capable of providing a composite oxide having a predetermined composition to be obtained in the step (2) described below. Examples thereof include a starting material of Mo, a starting material of V, a starting material of Nb, a starting material of X, and a starting material of Z. Note that, in the present embodiment, a solution containing at least a starting material of Sb for obtaining a formulated starting material liquid may be referred to as an "aqueous starting material liquid."

Examples of the method of dissolving or dispersing a starting material in water or a solvent include, but are not limited to, a method of dissolving or dispersing the material in water, and a method of dissolving or dispersing the material in a solvent, and the method of dissolving or dispersing the material in water is preferable. Additionally, the formulated starting material liquid includes, for example, a starting material of Mo, a starting material of V, a starting material of Nb, a starting material of Sb, a starting material of X, and a starting material of Z of which ratios have been adjusted so as to provide a composition of a composite oxide represented by the formula (1) obtained by the step (3) or (4) described below.

The starting material of Mo and the starting material of V are not particularly limited as long as the starting materials are a compound containing Mo and a compound containing V, respectively, and ammonium heptamolybdate [$(NH_4)_6Mo_7O_{24} \cdot 4H_2O$] and ammonium metavanadate [$NH_4VO_3$] can be suitably used, respectively.

The starting material of Nb is not particularly limited as long as the starting material is a compound containing Nb, and niobic acid, an inorganic acid salt of niobium, and an organic acid salt of niobium can be suitably used. Of these, niobic acid is preferable. Niobic acid is represented by $Nb_2O_5 \cdot nH_2O$ and referred to also as a niobium hydroxide or a niobium oxide hydrate. It is also preferable to use, as the starting material of Nb, a composition of a niobium compound and a dicarboxylic acid having a molar ratio of the dicarboxylic acid to niobium (dicarboxylic acid/niobium) of 1.0 or more and 4.0 or less. The dicarboxylic acid in this case is not particularly limited, but oxalic acid is preferable.

As the starting material of Sb, the antimony particles [$Sb_2O_3$] mentioned above are used.

The antimony particles to be used have an average particle size of 1.2 μm or less, preferably 0.8 μm or less, more preferably 0.4 μm or less. When the antimony particles have an average particle size of 1.2 μm or less, it is possible to increase the dissolution rate in an aqueous solvent, and thus, it is possible to obtain a more homogeneous aqueous starting material liquid. For this reason, when a composite oxide to be obtained is used as a catalyst, the yield of an unsaturated nitrile or unsaturated acid tends to increase. Also due to the increase in the solubility in an aqueous solvent, it is possible to prepare a catalyst with which a composite oxide having an increased antimony composition is obtained. From the viewpoint of handleability, the average particle size of diantimony trioxide is more preferably 0.1 μm or more.

A method for adjusting the average particle size of the antimony particles to 1.2 μm or less may be any method, for example, a method including pulverizing the particles to 1.2 μm or less with a wet ball mill. The average particle size of the antimony particles can be measured by any known method. Examples of the measurement method include a BET method, laser diffraction method, dynamic light scattering method, centrifugal sedimentation method, electrical sensing zone method, and electron photomicrograph method. More specifically, as described in Example mentioned below, the value of a median size measured by the laser diffraction method may be used as the average particle size of the antimony particles.

Furthermore, in the antimony particles in the present embodiment, the abundance of pentavalent antimony contained in the surface layer of the antimony particles (e.g., thickness: 2 nm) to be measured in XPS analysis is less than 70 atom %. That is, when the total amount of trivalent antimony and pentavalent antimony in the surface layer of the antimony particles (e.g., thickness: 2 nm) to be measured by the XPS method is set at 100 atom %, the abundance of pentavalent antimony is preferably less than 70 atom %, more preferably less than 68 atom %, still more preferably less than 65 atom %, even more preferably less than 60 atom %.

The lower limit of the abundance of pentavalent antimony is not particularly limited, but is preferably 0 atom %, for example.

The abundance of pentavalent antimony is calculated from the peak intensity of the pentavalent antimony $3d_{3/2}$ and the peak intensity of the trivalent antimony $3d_{3/2}$. A charge correction is carried out by setting the peak position of the C1s at 284.6 eV on the abscissa axis for Narrow scan.

After measurement of the relative intensities of trivalent antimony and pentavalent antimony, the pentavalent antimony ratio is calculated using the following expression (i):

Abundance of pentavalent antimony (atom %)=[a/(a+b)]×100       (i)

a: peak intensity of pentavalent antimony $3d_{3/2}$
b: peak intensity of trivalent antimony $3d_{3/2}$ Note that the peak positions of trivalent and pentavalent antimony may vary depending on various factors such as characteristics of XPS analysis and charge of a sample. Thus, the peak intensities are measured by taking the peak top around 540 eV as the peak position of the pentavalent antimony $3d_{3/2}$ and the side having an energy 1.2 eV lower than the peak top as the peak position of the trivalent antimony $3d_{3/2}$.

When the antimony particles are oxidized, pentavalent antimony tends to be generated on the surface thereof. It is considered that the amount of pentavalent antimony varies depending on the production conditions and storage conditions. Accordingly, some commercially available antimony particles satisfy the requirements of the present embodiment whereas other commercially available antimony particles do not satisfy the requirements. When commercially available antimony particles are used, sampled antimony particles are subjected to XPS measurement in accordance with the method described above. This enables selection of antimony particles satisfying the requirements of the present embodiment. The particles selected may be used as a starting material.

When commercially available antimony particles satisfying the requirements of the present embodiment are not easily available, antimony particles are prepared by a known method that enables the oxidation of the surface of particles to be suppressed, such as a wet method (see a literature "Japanese Patent No. 3383882"). The antimony particles thus produced, having a controlled abundance of pentavalent antimony on the surface of the particles, may be used.

When commercially available antimony particles are used, those having an average particle size of 1.2 μm or less and an abundance of pentavalent antimony in the surface layer of the particles of less than 70 atom % may be used as received. Even with an average particle size of more than 1.2 μm, those having an abundance of pentavalent antimony in the surface layer of the particles of less than 70 atom % may be used after pulverized such that the particles have an average particle size of 1.2 μm or less.

A composite oxide prepared using antimony particles having an abundance of pentavalent antimony of less than 70 atom % will exhibit a higher yield of an unsaturated nitrile or unsaturated acid, when used as a catalyst, than that of a composite oxide prepared using antimony particles having an abundance of pentavalent antimony of 70 atom % or more. The reason of this improvement in the yield is not clear, but inferred as follows (however, the mechanism is not limited thereto). The pentavalent antimony present on the surface of the antimony particles of the starting material is present in a trace amount relative to the total antimony, but the presence thereof promotes complete decomposition of propane or complete decomposition of an unsaturated nitrile or unsaturated acid caused by a composite oxide prepared to thereby decrease the yield. It is inferred that an abundance of pentavalent antimony of less than 70 atom % may suppress complete decomposition of propane or an unsaturated nitrile or unsaturated acid caused by a composite oxide prepared to thereby increase the yield of the unsaturated nitrile or unsaturated acid. That is, the abundance of pentavalent antimony herein referred to is an index indirectly representing the amount of pentavalent antimony contained in the antimony particles as the starting material. Thus, when optional pulverization is carried out before XPS measurement, internal trivalent antimony is exposed on the surface and the apparent ratio of pentavalent antimony is decreased. However, the total amount of pentavalent antimony is not changed. For this reason, even if the pentavalent antimony abundance of diantimony trioxide as the starting material is less than 70 atom % in XPS after the optional pulverization, the yield of an unsaturated nitrile or unsaturated acid will not increase when the composite oxide prepared by using the starting material is used as a catalyst. Accordingly, in the present embodiment, when adjustment of the particle size of antimony particles is required, those confirmed to have an abundance of pentavalent antimony of less than 70 atom % by XPS measurement, as an object, are preferably subjected to particle size adjustment. As mentioned above, the step (1) in the present embodiment can include, as required, a step (1-1) of providing antimony particles confirmed to have an abundance of pentavalent antimony of less than 70 atom % by XPS measurement, and a step (1-2) of adjusting the average particle size of the antimony particles to 1.2 μm or less.

Since pentavalent antimony is unlikely to dissolve in preparing an aqueous starting material liquid described below, it is considered that use of antimony particles having a low abundance of pentavalent antimony as the starting material improves the solubility compared with the case where antimony particles having a higher abundance of pentavalent antimony is used as the starting material. For this reason, the aqueous starting material liquid will be more homogeneous, and when a composite oxide to be obtained is used as a catalyst, the yield of an unsaturated nitrile or unsaturated acid tends to increase.

The starting material of X is not particularly limited as long as the starting material is a substance containing at least one element selected from the group consisting of W, Te, Bi, and Mn, and, for example, compounds containing these elements and substances obtained by solubilizing the metals of these elements with an appropriate reagent can be used. Examples of the compound containing these elements include, but are not limited to, ammonium salt, nitrate salt, carboxylate salt, carboxylic acid ammonium salt, peroxocarboxylate salt, peroxocarboxylic acid ammonium salt, halogenated ammonium salt, halide, acetylacetonate, and alkoxide, containing these elements. Of these, as the starting material of X, water-soluble starting materials, such as nitrate salt and carboxylate salt, containing these elements, are preferable, and ammonium metatungstate is more preferable.

The starting material of Z is not particularly limited as long as the starting material is a substance containing at least one element selected from the group consisting of La, Ce, Pr, Yb, Y, Sc, Sr, and Ba, and, for example, compounds containing these elements and substances obtained by solubilizing the metals of these elements with an appropriate reagent can be used. Examples of the compound containing these elements include, but are not limited to, nitrate salt, carboxylate salt, carboxylic acid ammonium salt, peroxocarboxylate salt, peroxocarboxylic acid ammonium salt, halogenated ammonium salt, halide, acetylacetonate, and alkoxide, containing these elements. Of these, water-soluble starting materials, such as nitrate salt and carboxylate salt, containing these elements are preferable.

A starting material of the silica contained in the carrier is not particularly limited, and for a part of or the whole of the silica starting material, silica sol and/or powder silica can also be used. Powder silica is preferably one produced by a pyrogenetic method. Use of powder silica dispersed in water in advance facilitates addition and mixing thereof to a slurry. A dispersing method is not particularly limited, and powder silica can be dispersed by using a common homogenizer, homomixer, ultrasonic vibrator or the like singly or in combination.

After each starting material is dissolved or dispersed in water or a solvent to obtain a formulated starting material liquid, the formulated starting material liquid obtained may be subjected to aging treatment. Aging of the formulated starting material liquid means that the formulated starting material liquid is left to stand or stirred for a predetermined time. An aging time is preferably 90 minutes or more and 50 hours or less, more preferably 90 minutes or more and 6 hours or less. With an aging time in the range described above, a formulated starting material liquid having a suitable redox state is more likely to be formed, and a composite oxide to be obtained tends to have more improved catalytic performance.

The temperature of the formulated starting material liquid in aging is preferably 25° C. or more and 65° C. or less. With the temperature being 25° C. or more, condensation of a Mo component and deposition of metal oxides caused by V and the other metal species or a plurality of metals can be prevented. With the temperature being 65° C. or less, hydrolysis of a complex containing Nb and hydrogen peroxide is prevented from excessively occurring, and a formulated starting material liquid in a preferable form tends to be prepared.

[Step (2): Drying Step]

The step (2) in the present embodiment dries the formulated starting material liquid obtained in the above step (1) to thereby obtain a dried material. Drying the formulated starting material liquid (e.g., a slurry) obtained via the step (1) may provide a dried material as a catalyst precursor. The drying can be carried out by a known method, for example, spray drying or evaporation to dryness.

When a fluidized-bed reaction mode is employed for the gas-phase catalytic ammoxidation reaction, from the viewpoint of making the flowability in a reactor to be in a satisfactory state and the like, it is preferable to obtain a microspherical dried material. In order to obtain the microspherical dried material, spray drying is preferably employed as the drying method. Atomization in the spray drying may be by any of a centrifugal mode, a twin fluid nozzle mode, and a high-pressure nozzle mode. A drying heat source to be used for spray drying includes air heated by steam, an electric heater or the like. The inlet temperature of a drier of an apparatus to be used for spray drying is preferably 150° C. or more and 300° C. or less, from the viewpoint of making the shape and/or strength of composite oxide particles obtained in the step (3) described below to be in a satisfactory state, improving the performance of the composite oxide to be obtained, and the like. Further, the outlet temperature of the drier is preferably 100° C. or more and 160° C. or less.

The spraying rate, the liquid feed rate of the formulated starting material liquid, the rotation frequency of an atomizer in the case of employing the centrifugal mode, and the like are only required to be adjusted depending on the size of the apparatus and such that the particle size of a dried material to be obtained falls within a suitable range. Specifically, the average particle size of the dried material is preferably 5.0 μm or more and 200 μm or less, more preferably 10 μm or more and 150 μm or less. The average particle size of the dried material is determined by measuring the particle size distribution in compliance with JIS R 1629-1997 "Determination of particle size distributions for fine ceramic raw powders by laser diffraction method" and averaging the measurement in terms of volume. In more detail, a portion of the dried material is calcined in air at 400° C. for 1 hour, and the particle size distribution of particles obtained as an object is measured by using a laser diffraction scattering particle size distribution analyzer (manufactured by Beckman Coulter, Inc., trade name: "LS230"). The reason that the average particle size is determined after the portion of the dried material is "calcined in air at 400° C. for 1 hour" is to prevent the dried material from being dissolved in water. In other words, "calcined in air at 400° C. for 1 hour" is solely for the measurement, and is irrelevant to the calcination step described below. It can be considered that the particle size does not substantially change before and after this calcination.

With respect to a method of measuring the average particle size of the dried material, more specifically, the measurement of the average particle size is carried out as follows in compliance with the manual attached to a laser diffraction scattering particle size distribution analyzer (manufactured by Beckman Coulter, Inc., trade name: "LS230"). First, a background measurement (RunSpeed60) is carried out, and thereafter, 0.2 g of particles is weighed in a screw tube of an appropriate size and 10 cc of water is added thereto. The screw tube is capped (hermetically sealed) and sufficiently shaken to disperse the particles in water. An ultrasonic wave of 300 W is applied by the analyzer to thereby shake the screw tube again sufficiently. Thereafter, the particles dispersed in water are injected in the analyzer body with a dropper so as to have a suitable concentration (concentration 10, PIDS 60), under continued application of the ultrasonic wave. When the concentration indication becomes stable, the application of the ultrasonic wave is suspended. The solution is left to stand for 10 seconds, and thereafter, the measurement is initiated (measurement time: 90 seconds). The value of a median size of the measurement result is taken as an average particle size.

For the purpose of preventing deposition of the catalyst precursor in the spray drying apparatus, the spray drying apparatus is preferably equipped with a vibrating machine to impart vibration to the spray drying apparatus or an apparatus for preventing a catalyst precursor from depositing such as an air knocker to impart impacts thereto. It is also preferable that the spray drying be once suspended at a suitable frequency and the interior of the apparatus be washed with water or the like.

The operating conditions of the air knocker provided in the drying apparatus can be adjusted optionally depending on the size of the apparatus, the thickness of the wall, or the degree of peeling of deposits. Examples of the operating conditions include the impact magnitude and the impact frequency of the air knocker, the increase and decrease of the number of the air knockers installed, and the alteration of the installation position(s). It is preferable that the impact magnitude of the air knocker be so strong as not to deform and damage the wall surface and/or other drying apparatus portions even in a long-term operation. From the similar viewpoint, the impact frequency is preferably one or more times in 1 minute, more preferably one or more times in 10 seconds. With respect to the number of the air knockers installed and the installation positions, it is preferable that the number be increased for portions where intense deposits are recognized by the observation of the interior after the long-term operation, knockers on portions where substantially no deposits are recognized be transferred to portions where intense deposits are recognized, and the like.

The dried material may contain ammonium, an organic acid, an inorganic acid and the like, in addition to moisture.

[Step (3): Calcination Step]

The step (3) in the present embodiment is a step of calcining the dried material obtained in the step (2) to thereby obtain a calcined material.

As an apparatus for calcination (hereinafter, referred to also as "calcining device"), which is not particularly limited to the following, for example, a rotary furnace (rotary kiln) can be used. The shape of the calcining device is not particularly limited. From the viewpoint of enabling continuous calcination to be carried out, the shape is preferably tubular (calcining tube), and, in particular, more preferably cylindrical. A heating mode to heat the calcining device is preferably an external heating mode, from the viewpoint of easily regulating the calcination temperature so as to make a favorable temperature-elevation pattern, and the like, and an electric oven can be suitably used. The size and material of the calcining tube can be selected appropriately depending on the calcination conditions and the amount calcined.

The material of the calcining device is not particularly limited as long as the material preferably has heat resistance and has enough strength to prevent the calcining device from being broken by impact, and for example, heat-resistant glass and SUS can suitably be used.

The calcining tube can be also partitioned into two or more zones by installing therein a weir plate having a hole to pass the powder through on its center perpendicularly (or substantially perpendicularly) to the flow of the powder. The residence time of the powder in the calcination tube can be taken more easily by installation of the weir plate. The number of the weir plate(s) may be one or two or more.

For preventing breaking, cracking, or the like in the dried material as well as for homogeneous calcination, it is preferable that the dried material be calcined while the calcining tube is rotated with its longitudinal direction as its axis.

In the calcination of the dried material, from the viewpoint of bringing a composite oxide to be obtained into in a satisfactory redox state, improving the performance of the composite oxide, and the like, with respect to the heating temperature of the dried material, it is preferable that raising of the temperature be started from a temperature lower than 400° C. and be kept on continuously or stepwise up to a temperature in the range of 550° C. or more and 800° C. or less.

The calcination atmosphere may be in an air atmosphere or under an air circulation. From the viewpoint of easily adjusting the composite oxide into a satisfactory redox state, and the like, it is preferable that at least a part of the calcination step be carried out under a flow of an inert gas, such as nitrogen, containing substantially no oxygen.

In the case of carrying out the calcination in a batch mode, from the viewpoint of adjusting the oxide into a satisfactory redox state, the volume of the inert gas to be supplied is, per 1 kg of the dried material, preferably 50 NL/hr or more, more preferably 50 NL/hr or more and 5,000 NL/hr or less, still more preferably 50 NL/hr or more and 3,000 NL/hr. Herein, "NL" means the standard temperature and pressure conditions, that is, a volume (L) measured at 0° C. and 1 atm.

In the case of carrying out the calcination in a continuous mode, from the viewpoint of adjusting the oxide into a satisfactory redox state, the volume of the inert gas to be supplied is, per 1 kg of the dried material, preferably 50 NL/hr or more, more preferably 50 NL/hr or more and 5,000 NL/hr or less, still more preferably 50 NL/hr or more and 3,000 NL/hr or less. At this time, the contact form of the inert gas with the dried material may be counter-current contact or concurrent contact, but in consideration of gas components evolved from the dried material and air possibly mingling in a minute amount in the dried material, the counter-current contact is preferable.

In the case of calcining the dried material under a flow of an inert gas containing substantially no oxygen, when the dried material evaporates, decomposes, or otherwise, the constituent elements of a composite oxide contained therein are reduced. When the constituent elements of the composite oxide contained in the dried material have their substantially highest oxidation numbers, bringing the reduction ratio of the composite oxide in a desired range is industrially simple because it is only required to perform reduction in the step (3).

[Step (4): Projection Removal Step]

The step (4) in the present embodiment is a step of removing a projection present on the surface of particles of the calcined material obtained in the step (3). Many of projections are projecting oxide crystals and other impurities. Particularly, in the case of a calcined material containing a plurality of metals, the oxide having a composition different from that of the crystal forming a major part of the calcined material may be formed in such a shape that the oxide effuses from the main body of the calcined material. Such projections may cause a decrease in the flowability. Thus, removal of the projections from the catalyst surface tends to improve the catalytic performance. When the projections are removed on a gram scale, the following apparatus can be used. That is, a vertical tube can be used, wherein a perforated plate having one or more holes is provided in the bottom, and a paper filter is provided in the upper part. The calcined material is placed in this vertical tube, and air is circulated from the lower part. Therefore, an air current flows from each hole, to facilitate the contact among the calcined materials, and thereby the projections are removed.

[Method for Producing Unsaturated Nitrile and Unsaturated Acid]

The method for producing an unsaturated nitrile of the present embodiment comprises a step of obtaining an oxide catalyst by the method for producing an oxide catalyst according to the present embodiment, and a production step of subjecting propane or isobutane and $NH_3$ to a gas-phase catalytic ammoxidation reaction in the presence of the oxide catalyst obtained to obtain an unsaturated nitrile. The method for producing an unsaturated acid of the present embodiment comprises a step of obtaining an oxide catalyst by the method for producing an oxide catalyst according to the present embodiment, and a production step of subjecting propane or isobutane to a gas-phase catalytic oxidation reaction in the presence of the oxide catalyst obtained to obtain an unsaturated acid. As a specific example, a method will be described in which a gas-phase catalytic ammoxidation reaction of propane is carried out by bringing propane, ammonia, and an oxygen-containing starting material gas into contact with an oxide catalyst contained in a reactor to thereby produce a corresponding unsaturated nitrile. In the method for producing an unsaturated acid, a gas-phase catalytic oxidation reaction of propane is carried out by bringing propane and an oxygen-containing starting material gas into contact with an oxide catalyst contained in a reactor to thereby produce a corresponding unsaturated acid.

Propane and ammonia are not limited to highly-pure ones, and it is possible to use propane containing 5.0% by volume or less impurities such as ethane, ethylene, n-butane and isobutane; ammonia containing 1.0% by volume or less impurities such as water; and an industrial-grade propane gas and ammonia gas.

Examples of the oxygen-containing starting material gas include, but are not particularly limited to, air, air enriched with oxygen, pure oxygen; and these gases diluted with an inert gas such as helium, argon, carbon dioxide or nitrogen, or steam. Of these, in the case of an industrial-scale use, air is preferably used because of its simplicity.

Examples of the reaction system include reaction systems of fixed bed, fluidized bed and moving bed, but from the viewpoint of heat removal of a reactor, the reaction system of fluidized bed is preferable.

The reaction temperature is preferably 350° C. or more and 500° C. or less, more preferably 380° C. or more and 470° C. or less. When the reaction temperature is 350° C. or more, an ammoxidation reaction of propane tends to be able to proceed at a practical rate; and when the reaction temperature is 500° C. or less, the decomposition of an intended product tends to be able to be suppressed.

With a lower reaction pressure, the selectivity of an unsaturated nitrile tends to be satisfactory, and the reaction pressure is preferably $0.3 \times 10^5$ Pa or more and $5.0 \times 10^5$ Pa or less, more preferably $0.5 \times 10^5$ Pa or more and $3.0 \times 10^5$ Pa or less.

A contact time is preferably 0.1 to 10 (sec·g/cm$^3$), more preferably 0.5 to 5 (sec·g/cm$^3$). With the contact time in this range, the generation of by-products tends to be able to be further suppressed and the yield of an unsaturated nitrile tends to be able to be further improved.

In the present embodiment, the contact time is defined by the following equation:

$$\text{Contact time (sec·g/cm}^3\text{)} = (W/F) \times 273/(273+T)$$

wherein W, F, and T are defined as follows:
W=Amount of catalyst filling the reactor (g)
F=Flow rate (Ncm/sec) of a starting material mixed gas under standard conditions (0° C., $1.013 \times 10^5$ Pa)
T=Reaction temperature (° C.)

The reaction mode may be of a recycle type in which an unreacted starting material gas is recovered and supplied again to the reactor, or may be of a single-current type in which the starting material gas is not recycled, but a preferable compositional ratio of the starting material gas differs depending on the reaction mode. For example, in the case of the reaction in the single-current type, since the conversion ratio of propane is required to be high, the molar ratio of oxygen to propane (oxygen/propane) is preferably 0.5 or more and 4.5 or less, more preferably 1.0 or more and 4.0 or less, still more preferably 1.5 or more and 3.5 or less. In contrast, in the case of recycling unreacted propane, in order to increase the selectivity of a corresponding unsaturated nitrile, a condition leading to suppress the conversion ratio of propane low is preferable. Thus, the molar ratio (oxygen/propane) is preferably 0.2 or more and 3.5 or less, more preferably 0.6 or more and 3.0 or less, still more preferably 1.0 or more and 2.5 or less. However, the compositional ratio of the starting material gas may affect the outlet oxygen concentration, and thus, in either reaction mode, the compositional ratio is preferably determined by concurrently taking it into consideration that the outlet oxygen concentration falls within a desired range.

As mentioned above, according to the method for producing an oxide catalyst and the method for producing an unsaturated nitrile using an oxide catalyst obtained therefrom according to the present embodiment, it is possible to obtain an unsaturated nitrile and unsaturated acid from propane at a high yield. More specifically, it is possible to obtain acrylonitrile or acrylic acid from propane at a high yield.

EXAMPLES

Hereinafter, the present embodiment will be described in more detail by way of specific Examples and Comparative Examples, but the present embodiment is not limited in any way to these Examples and Comparative Examples unless departing from its gist. Evaluations carried out in Examples and Comparative Examples described below were measured by the following methods.

(Evaluation) AN Yield

In Examples and Comparative Examples, the yield of acrylonitrile (hereinafter, AN) (indicated simply as "Yield" in Table 1) was determined as follows. The molar number of AN produced was measured by previously taking a calibration curve by a measurement using gas chromatography (GC) of an AN gas having an already-known concentration, and thereafter, quantitatively injecting a gas produced by an ammoxidation reaction into GC. The yield of AN was calculated based on the following equation from the "molar number of AN produced" obtained by the measurement. The results are shown in Table 1.

Yield of AN (%)=(molar number of AN produced)/(molar number of propane supplied)×100

Commercially available antimony particles (antimony trioxide) of different average particle sizes in a plurality of grades and a plurality of lots were obtained and subjected to XPS measurement using an ESCALAB 250 manufactured by Thermo Fisher Scientific K.K. The measurement was carried out by using monochromated AlK$_\alpha$-rays as the X-rays and an X-ray output at 15 kV×10 mA. For the Dwell time, Survey scan: 100 eV and Narrow scan: 20 eV were used. Neutralization conditions included Filament Current of the neutralization gun set at 3 A and Filament Bias set at 3 V. The carbon 1 s peak was measured in a measurement range of 296 to 286 eV, with a step width of 0.1 eV and a cumulative number of 50. The oxygen 1 s peak and the antimony 3d peak were measured in the same manner as for the carbon 1 s peak except that the measurement range was 550 to 522 eV and the cumulative number was 30. In order to calculate the abundance of pentavalent antimony in the surface layer of the antimony particles (thickness: 2 nm), software Avantage accompanying the above XPS analyzer was used, and a charge correction was carried out such that the carbon 1 s peak was located at 284.6 eV. The position of the peak top around 540 eV was at 539.8 eV, which was defined as the peak position of the pentavalent antimony 3d$_{3/2}$, and 538.6 eV, which was the side having an energy 1.2 eV lower than the peak top, was defined as the peak position of the trivalent antimony $3d_{3/2}$. From each peak intensity thus determined, the abundance of pentavalent antimony was calculated based on the following equation:

Abundance of pentavalent antimony (atom %)=[$a$/($a$+$b$)]×100　　(i)

a: peak intensity of pentavalent antimony $3d_{3/2}$
b: peak intensity of trivalent antimony $3d_{3/2}$ The average particle size of each antimony particle (hereinafter, simply referred to also as "particle size.") was also measured by the laser diffraction method. At this time, by using an analyzer, trade name "LS230", manufactured by Beckman Coulter, Inc., the measurement was carried out as follows, in compliance with to the manual attached to the analyzer. First, a background measurement (RunSpeed60) is carried out, and thereafter, 0.2 g of antimony particles was weighed in a screw tube of an appropriate size and 10 cc of water was added thereto. The screw tube was capped (hermetically sealed) and sufficiently shaken to disperse the antimony particles in water. Subsequently, an ultrasonic wave of 300 W was applied by the analyzer to thereby shake the screw tube again sufficiently. Thereafter, the antimony particles dispersed in water were injected in the analyzer body with a dropper so as to have a suitable concentration (concentration 10, PIDS 60), under continued application of the ultrasonic wave. When the concentration indication became stable, the application of the ultrasonic wave was suspended. The solution was left to stand for 10 seconds, and thereafter, the measurement was initiated (measurement time: 90 seconds). The value of a median size of the measurement result was taken as the average particle size of antimony particles.

The composition of the oxide catalyst was measured by X-ray fluorescence analysis (trade name "RIX1000" manufactured by Rigaku Corporation, Cr tube, tube voltage: 50 kV, tube current: 50 mA).

The amount of the carrier was determined, as the amount of the carrier based on the total amount of the oxide catalyst (100% by mass) obtained in each of Examples and Comparative Examples described below, by measuring the oxide catalyst obtained by X-ray fluorescence analysis (trade name "RIX1000" manufactured by Rigaku Corporation, Cr tube, tube voltage: 50 kV, tube current: 50 mA).

Example 1

(Step (1): Formulation Step)

Based on the results of the XPS measurement and particle size measurement mentioned above, antimony particles having an abundance of pentavalent antimony (in the table, abbreviated as "pentavalent ratio.") of 67 atom % and an average particle size of 0.67 μm were selected from commercially available antimony particles (antimony trioxide). The XPS chart obtained at that time is shown in FIG. 1.

An oxide catalyst of a feed composition formula represented by $Mo_{1.000}V_{0.189}Sb_{0.242}Nb_{0.116}W_{0.032}Ce_{0.009}O_n$/49 wt %-$SiO_2$ was prepared by the following method.

First, 410.9 g of ammonium heptamolybdate [$(NH_4)_6Mo_7O_{24}\cdot 4H_2O$], 51.1 g of ammonium metavanadate [$NH_4VO_3$], 81.6 g of the antimony particles of Example 1 [$Sb_2O_3$], and 9.2 g of cerium nitrate hexahydrate [Ce$(NO_3)_3\cdot 6H_2O$] were added to 2447 g of water, and the resulting mixture was heated at 95° C. for an hour under stirring to obtain an aqueous starting material liquid (I).

A niobium-mixed liquid was prepared by the following method.

Into 5640 g of water, 795.1 g of niobic acid containing 80.2% by mass in terms of $Nb_2O_5$ and 3120 g of oxalic acid dihydrate [$H_2C_2O_4\cdot 2H_2O$] were mixed. The molar ratio of the oxalic acid/niobium fed was 5.24, and the concentration of the niobium fed was 0.50 (mol-Nb/kg-liquid). This liquid was heated and stirred at 95° C. for 2 hours to thereby obtain a mixed liquid in which niobium was dissolved. The mixed liquid was left to stand, and cooled with ice. Thereafter, the solid was filtered off by suction filtration to thereby obtain a homogeneous niobium-mixed liquid. The molar ratio of oxalic acid/niobium of the niobium-mixed liquid was 2.31 according to the following analysis.

10 g of the niobium-mixed liquid was precisely weighed in a crucible, dried at 95° C. overnight, and thereafter heat-treated at 600° C. for an hour to thereby obtain 0.8796 g of $Nb_2O_5$. From this result, the niobium concentration was 0.662 (mol-Nb/kg-liquid). In a 300-mL glass beaker, 3 g of the niobium-mixed liquid was precisely weighed, and 200 mL of hot water at about 80° C. was added thereto. Then, 10 mL of a 1:1 sulfuric acid was added to the solution. The mixed liquid obtained was titrated under stirring by using a ¼ N $KMnO_4$, while being held at a liquid temperature of 70° C. on a hot stirrer. A point where a faint pinkish color due to $KMnO_4$ continued for about 30 seconds or more was taken as the end point. The concentration of oxalic acid was, as a result of a calculation by the following formula from the titer, 1.531 (mol-oxalic acid/kg).

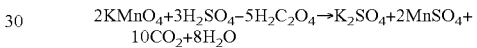

The niobium-mixed liquid obtained was used as a niobium starting material liquid ($B_0$) in the preparing of the following composite oxide.

To 404.4 g of the niobium-mixed liquid ($B_0$), 60.7 g of a hydrogen peroxide aqueous solution containing 30% by mass of $H_2O_2$ was added, and the solution was stirred and mixed at room temperature for 10 minutes to thereby prepare an aqueous starting material liquid (II).

The aqueous starting material liquid (I) obtained was cooled down to 70° C., and then, 720.6 g of a silica sol containing 34.0% by mass of $SiO_2$ was added to the liquid. Furthermore, 95.1 g of a hydrogen peroxide aqueous solution containing 30% by mass of $H_2O_2$ was added thereto, and the solution was continuously stirred at 55° C. for 30 minutes. Then, the aqueous starting material liquid (II), 34.1 g of an ammonium metatungstate aqueous solution containing 50% by mass of $WO_3$, and 2450.0 g of a dispersion liquid in which a powder silica was dispersed at a concentration of 10 wt % in water were added successively to the solution to thereby obtain an aqueous mixed liquid (III). The aqueous mixed liquid (III) was aged, after the addition of the aqueous starting material liquid (II), at 50° C. for 2 hours and 30 minutes to thereby obtain a formulated starting material liquid (slurry (A)).

(Step (2): Drying Step)

The slurry (A) obtained was supplied to and dried in a centrifugal-type spray drier to thereby obtain a microspherical dried material. The inlet air temperature of the drier was 210° C., and the outlet air temperature thereof was 120° C. The drying operation was repeated several times.

(Step (3): Calcination Step)

A cylindrical calcining tube made of SUS having a diameter of 3 inches was filled with 500 g of the dried material obtained. The dried material was calcined at 680° C. for 2 hours under a nitrogen gas flow at 2.0 NL/min with the tube being rotated to thereby obtain a calcined material.

(Step (4): Projection Removal Step)

In a vertical tube (inner diameter: 41.6 mm, length: 70 cm) equipped with a perforated disc having 3 holes of 1/64 inches in diameter at the bottom and a paper filter at the upper part, 50 g of the calcined material obtained above was placed. Subsequently, air was allowed to flow at room temperature upward from the lower part of the vertical tube via each hole to promote the contact among the calcined material particles. At this time, the air flow length in the flow direction of the air flow was 56 mm, and the average linear velocity of the air flow was 332 m/s. The oxide catalyst obtained 24 hours later had no projection.

(Ammoxidation Reaction of Propane)

A Vycor glass fluidized bed-type reaction tube having an inner diameter of 25 mm was filled with 45 g of the catalyst obtained. A gas having a molar ratio of propane:ammonia:oxygen:helium=1:0.9:2.0:5.6 was supplied to the reaction tube at a reaction temperature of 445° C. and at normal pressure as the reaction pressure so as to achieve a contact time of 3.0 sec·g/cc. The reaction results obtained are shown in Table 1.

Examples 2 to 4

Catalysts were prepared under the same conditions as in Example 1 and the ammoxidation reaction of propane was carried out except that antimony particles having a particle size of 0.38 μm and a pentavalent antimony abundance of 68 atom %, antimony particles having 0.68 μm and 69 atom %, and antimony particles having 1.18 μm and 65 atom % were each selected from commercially available antimony particles (diantimony trioxide) based on the results of the XPS measurement and particle size measurement and the particles selected were used as the starting material. The results are each shown in Table 1.

Example 5

With reference to the example of Japanese Patent No. 3383882, antimony particles same as the "particulate antimony trioxide" were prepared in the same manner by a wet method. As a result of the XPS measurement and particle size measurement on the antimony particles, the particle size was 4.03 μm and the pentavalent antimony abundance was 24 atom %. The antimony particles were subjected to pulverizing treatment using a ball mill to reduce the particle size to 1.05 μm. A catalyst was prepared under the same conditions as in Example 1 and the ammoxidation reaction of propane was carried out except that these antimony particles were used as the starting material. The results are each shown in Table 1.

Example 6

An oxide catalyst of a feed composition formula represented by $Mo_{1.000}V_{0.160}Sb_{3.230}Nb_{0.114}W_{0.032}Ce_{0.009}O_n$/49 wt %-$SiO_2$ was prepared by the following method, using the antimony particles and niobium-mixed liquid ($B_0$) used in Example 1.

419.7 g of ammonium heptamolybdate [$(NH_4)_6Mo_7O_{24}\cdot4H_2O$], 44.2 g of ammonium metavanadate [$NH_4VO_3$], 79.2 g of the antimony particles prepared in Example 1 [$Sb_2O_3$], and 9.4 g of cerium nitrate hexahydrate [$Ce(NO_3)_3\cdot6H_2O$] were added to 2447 g of water, and the solution was heated at 95° C. for an hour under stirring to obtain an aqueous starting material liquid (IV).

To 406.6 g of the niobium-mixed liquid ($B_0$), 61.0 g of a hydrogen peroxide aqueous solution containing 30% by mass of $H_2O_2$ was added, and the solution was stirred and mixed at room temperature for 10 minutes to thereby prepare an aqueous starting material liquid (V).

The aqueous starting material liquid (IV) obtained was cooled down to 70° C., and then, 720.6 g of a silica sol containing 34.0% by mass of $SiO_2$ was added to the liquid. Furthermore, 92.3 g of a hydrogen peroxide aqueous solution containing 30% by mass of $H_2O_2$ was added thereto, and the solution was continuously stirred at 55° C. for 30 minutes. Then, the aqueous starting material liquid (V), 34.8 g of an ammonium metatungstate aqueous solution containing 50% by mass of $WO_3$, and 2450.0 g of a dispersion liquid in which a powder silica was dispersed at a concentration of 10 wt % in water were added successively to the solution to thereby obtain an aqueous mixed liquid (VI). The aqueous mixed liquid (VI) was aged, after the addition of the aqueous starting material liquid (V), at 50° C. for 2 hours and 30 minutes to thereby obtain a formulated starting material liquid (slurry (B)).

A catalyst was prepared under the same conditions as in Example 1 and the ammoxidation reaction of propane was carried out except that a slurry (B) was obtained by the method as above. The results are each shown in Table 1.

Comparative Example 1

A catalyst was prepared under the same conditions as in Example 1 and the ammoxidation reaction of propane was carried out except that antimony particles having a particle size of the antimony particles of 1.15 μm and a pentavalent antimony abundance of 70 atom % were selected and obtained from commercially available antimony particles (diantimony trioxide) based on the results of the XPS measurement and particle size measurement and the particles selected were used as the starting material.

The results are shown in Table 1. The XPS chart of the antimony is shown in FIG. 2.

Comparative Example 2

A catalyst was prepared under the same conditions as in Example 1 and the ammoxidation reaction of propane was carried out except that antimony particles having a particle size of the antimony particles of 0.50 μm and a pentavalent antimony abundance of 71 atom % were selected and obtained from commercially available antimony particles (diantimony trioxide) based on the results of the XPS measurement and particle size measurement and the particles selected were used as the starting material. The results are shown in Table 1.

Comparative Example 3

A catalyst was prepared under the same conditions as in Example 1 and the ammoxidation reaction of propane was carried out except that antimony particles having a particle size of the antimony particles of 1.52 μm and a pentavalent antimony abundance of 65 atom % were selected and obtained from commercially available antimony particles (diantimony trioxide) based on the results of the XPS measurement and particle size measurement and the particles selected were used as the starting material. The results are shown in Table 1.

Comparative Example 4

A catalyst was prepared under the same conditions as in Example 1 and the ammoxidation reaction of propane was carried out except that antimony particles having a particle size of the antimony particles of 1.40 μm and a pentavalent antimony abundance of 72 atom % were selected and obtained from commercially available antimony particles (diantimony trioxide) based on the results of the XPS measurement and particle size measurement and the particles selected were used as the starting material. The results are shown in Table 1.

Comparative Example 5

A catalyst was prepared under the same conditions as in Example 1 and the ammoxidation reaction of propane was carried out except that the wet-method antimony particles prepared in Example 5 were used without pulverizing treatment, as the starting material. The results are each shown in Table 1.

Comparative Example 6

A catalyst was prepared under the same conditions as in Example 5 and the ammoxidation reaction of propane was carried out except that the antimony particles having a particle size of 1.15 μm and a pentavalent antimony abundance of 70 atom %, which were used in Comparative Example 1, were used as the starting material. The results are shown in Table 1.

TABLE 1

| | Particle size (μm) | Pentavalent ratio (atom %) | Slurry | Yield (%) |
|---|---|---|---|---|
| Example 1 | 0.67 | 67 | A | 53.8 |
| Example 2 | 0.38 | 68 | A | 53.9 |
| Example 3 | 0.68 | 69 | A | 53.4 |
| Example 4 | 1.18 | 65 | A | 53.6 |
| Example 5 | 1.05 | 24 | A | 54.2 |
| Example 6 | 0.67 | 67 | B | 53.5 |
| Comparative Example 1 | 1.15 | 70 | A | 52.2 |
| Comparative Example 2 | 0.50 | 71 | A | 52.5 |
| Comparative Example 3 | 1.52 | 65 | A | 52.6 |
| Comparative Example 4 | 1.40 | 72 | A | 52.1 |
| Comparative Example 5 | 4.03 | 24 | A | 52.3 |
| Comparative Example 6 | 1.15 | 70 | B | 51.7 |

The present application is based on Japanese Patent Application (Japanese Patent Application No. 2016-158858), filed in Japan Patent Office on Aug. 12, 2016, the contents of which are hereby incorporated by reference.

INDUSTRIAL APPLICABILITY

The method for producing an oxide catalyst of the present invention can be used for production of a catalyst for production of an unsaturated nitrile.

The invention claimed is:

1. A method for producing an oxide catalyst comprising antimony, comprising
obtaining the oxide catalyst using an antimony particle comprising a diantimony trioxide as a source of the antimony, by a process including the steps of:
step (1): dissolving or dispersing a starting material containing the antimony particle to thereby obtain a formulated starting material liquid,
step (2): drying the formulated starting material liquid to thereby obtain a dried material,
step (3): calcining the dried material to thereby obtain a calcined material, and
step (4): removing projections present on the particle surface of the calcined material to thereby obtain a main body of the oxide catalyst;
wherein an abundance of a pentavalent antimony in a 2 nm surface layer of the antimony particle to be measured in XPS analysis is less than 70 atom %, and
the antimony particle has an average particle size of 1.2 μm or less,
wherein, the obtained oxide catalyst is represented by following formula (1):

$$Mo_1V_aNb_bSb_cX_dZ_eO_n \quad (1)$$

wherein X represents at least one element selected from the group consisting of W, Bi, Mn, and Ti; Z represents at least one element selected from the group consisting of La, Ce, Pr, Yb, Y, Sc, Sr, and Ba; a, b, c, d, e, and n represent atomic ratios of respective elements, and $0.01 \le a \le 1.00$, $0.01 \le b \le 1.00$, $0.01 \le c \le 1.00$, $0.00 \le d \le 1.00$, $0.00 \le e \le 1.00$; and n is a value satisfying balance among a valence.

2. The method for producing the oxide catalyst according to claim 1, wherein an oxide catalyst further comprising 20 to 70% by mass of silica, in terms of $SiO_2$, is obtained.

3. A method for producing an unsaturated nitrile, comprising a step of obtaining an oxide catalyst by the method for producing the oxide catalyst according to claim 1, and a production step of subjecting propane or isobutane and $NH_3$ to a gas-phase catalytic ammoxidation reaction in the presence of the oxide catalyst obtained to obtain the unsaturated nitrile.

4. A method for producing an unsaturated acid, comprising a step of obtaining an oxide catalyst by the method for producing the oxide catalyst according to claim 1, and a production step of subjecting propane or isobutane to a gas-phase catalytic oxidation reaction in the presence of the oxide catalyst obtained to obtain the unsaturated acid.

5. A method for producing an unsaturated nitrile, comprising a step of obtaining an oxide catalyst by the method for producing the oxide catalyst according claim 2, and a production step of subjecting propane or isobutane and $NH_3$ to a gas-phase catalytic ammoxidation reaction in the presence of the oxide catalyst obtained to obtain the unsaturated nitrile.

6. A method for producing an unsaturated acid, comprising a step of obtaining an oxide catalyst by the method for producing the oxide catalyst according to claim 2, and a production step of subjecting propane or isobutane to a gas-phase catalytic oxidation reaction in the presence of the oxide catalyst obtained to obtain the unsaturated acid.

7. The method for producing the oxide catalyst according to claim 1, wherein
the range of the abundance of a pentavalent antimony in a 2 nm surface layer of the antimony particle is 24 atom % or more and 69 atom % or less; and/or
the range of the average particle size of antimony particles is 0.38 μm or more and 1.18 μm or less.

8. The method for producing the oxide catalyst according to claim 1, wherein, in the formula (1), $0.01 \le a \le 0.189$.

9. The method for producing the oxide catalyst according to claim 1, wherein, in the formula (1), $0.02 \le b \le 0.70$ or $0.03 \le b \le 0.40$.

10. The method for producing the oxide catalyst according to claim 1, wherein, in the formula (1), $0.03 \leq c \leq 0.80$ or $0.05 \leq c \leq 0.50$.

11. The method for producing the oxide catalyst according to claim 1, wherein, in the formula (1), $0.001 \leq d \leq 0.50$ or $0.003 \leq d \leq 0.40$ or $0.005 \leq d \leq 0.30$.

12. The method for producing the oxide catalyst according to claim 1, wherein, in the formula (I), $0.0001 \leq e \leq 0.50$ or $0.0005 \leq e \leq 0.30$.

13. The method for producing the oxide catalyst according to claim 1, wherein, in formula (I), $0.50 \leq (a/c) \leq 2.00$ or $0.60 \leq (a/c) \leq 1.80$ or $0.70 \leq (a/c) \leq 1.60$.

\* \* \* \* \*